(12) United States Patent
Myllykangas et al.

(10) Patent No.: US 11,682,856 B2
(45) Date of Patent: Jun. 20, 2023

(54) HOLDER APPARATUS OF BIO-SIGNAL DEVICE AND METHOD OF ASSEMBLING HOLDER APPARATUS

(71) Applicant: BITTIUM BIOSIGNALS OY, Kuopio (FI)

(72) Inventors: Juha Myllykangas, Kuopio (FI); Mikko Määtänniemi, Kuopio (FI)

(73) Assignee: BITTIUM BIOSIGNALS OY, Kuopio (FI)

( * ) Notice: Subject to any disclaimer, the term of this patent is extended or adjusted under 35 U.S.C. 154(b) by 263 days.

(21) Appl. No.: 17/151,909

(22) Filed: Jan. 19, 2021

(65) Prior Publication Data
US 2022/0231449 A1    Jul. 21, 2022

(51) Int. Cl.
*H01R 13/52*    (2006.01)
*A61B 5/25*    (2021.01)
(Continued)

(52) U.S. Cl.
CPC ........... *H01R 13/5224* (2013.01); *A61B 5/25* (2021.01); *H01R 13/5219* (2013.01); *H01R 33/965* (2013.01); *H01R 33/97* (2013.01); *H01R 43/005* (2013.01); *H01R 43/18* (2013.01); *A61B 5/28* (2021.01); *A61B 5/291* (2021.01); *A61B 2562/12* (2013.01); *A61B 2562/227* (2013.01)

(58) Field of Classification Search
CPC ........... H01R 13/5224; H01R 13/5216; H01R 13/5219; H01R 33/965; H01R 33/97; H01R 43/18; A61B 5/25; A61B 5/291; A61B 5/28; A61B 2562/12; A61B 2562/227
See application file for complete search history.

(56) References Cited

U.S. PATENT DOCUMENTS

| 2013/0267809 A1 | 10/2013 | Brister et al. |
| 2018/0205172 A1* | 7/2018 | Zhao ............... H01R 13/5219 |
| 2019/0334304 A1 | 10/2019 | Myllykangas et al. |

FOREIGN PATENT DOCUMENTS

| EP | 3 714 781 | 9/2020 |
| WO | WO-2015182049 A1 * | 12/2015 ............. H01R 13/52 |

OTHER PUBLICATIONS

Extended European Search Report dated Jun. 22, 2022 in corresponding European Application No. 22151758.4, 8 pages.

\* cited by examiner

*Primary Examiner* — Oscar C Jimenez
*Assistant Examiner* — Paul D Baillargeon
(74) *Attorney, Agent, or Firm* — Nixon & Vanderhye PC

(57) ABSTRACT

A holder apparatus of a bio-signal device comprises a holder, which comprises a pocket for a bio-signal processing device, an extension with a hollow, the hollow and the pocket forming a continuous cavity through the holder, a connector, and an elastic seal with a hole. A shape of the elastic seal is matched with a shape of the hollow of the extension at an interface of the pocket, and the hollow and a shape of the hole is matched with a shape of the connector for sealing an interface between the connector and the holder while the connector and the elastic seal are within the hollow and the connector is in contact with the elastic seal. Sealant filler fills the hollow of the extension and is in physical contact with the connector, which is in the hollow against the seal, the elastic seal and the sealant filler allowing the connector to mate electrically with a counter-connector moved within the cavity in a direction from the pocket toward the hollow.

10 Claims, 4 Drawing Sheets

(51) Int. Cl.
*H01R 33/965* (2006.01)
*H01R 33/97* (2006.01)
*H01R 43/00* (2006.01)
*H01R 43/18* (2006.01)
*A61B 5/291* (2021.01)
*A61B 5/28* (2021.01)

HOLDER APPARATUS OF BIO-SIGNAL DEVICE AND METHOD OF ASSEMBLING HOLDER APPARATUS

FIELD

The invention relates to a holder apparatus of a bio-signal device and a method of assembling the holder apparatus.

BACKGROUND

An electronic device, which measures bio-signals such as ECG (ElectroCardioGram) and EEG (ElectroEncephaloGram), must be well contacted with the electrodes that are in contact with the body and mechanically reliably fixed to its support.

A bio-signal processing device can be inserted in and removed from a holder, which may be made of polymer. The holder includes an electrically conductive contact structure at its rear section for having an electric contact with electrodes and/or sensors that measure the bio-signals from the body.

A construct and final assembly of this kind of holder with the electrically conductive contact structure for disposable electrodes should be simple, save energy and material(s), have a low number of phases of assembly and keep assembly cost at minimum.

Attempts of reaching this goal include over-molding the holder with the electrically conductive contact structure or use special jig that grab, seal and hold the holder and the electrically conductive contact structure assembly at a correct position when liquid form sealant is poured into the assembly. Both of these processes are slow, costly and problems in yield are inevitable. Hence, an improvement would be welcome.

BRIEF DESCRIPTION

The present invention seeks to provide an improvement in the structure and the assembly.

The invention is defined by the independent claims. Embodiments are defined in the dependent claims.

LIST OF DRAWINGS

Example embodiments of the present invention are described below, by way of example only, with reference to the accompanying drawings, in which FIGS. 1A and 1B illustrate examples of a holder apparatus;

DESCRIPTION OF EMBODIMENTS

The following embodiments are only examples. Although the specification may refer to "an" embodiment in several locations, this does not necessarily mean that each such reference is to the same embodiment(s), or that the feature only applies to a single embodiment. Single features of different embodiments may also be combined to provide other embodiments. Furthermore, words "comprising" and "including" should be understood as not limiting the described embodiments to consist of only those features that have been mentioned and such embodiments may also contain features/structures that have not been specifically mentioned. All combinations of the embodiments are considered possible if their combination does not lead to structural or logical contradiction.

It should be noted that while Figures illustrate various embodiments, they are simplified diagrams that only show some structures and/or functional entities. The connections shown in the Figures may refer to logical or physical connections. It is apparent to a person skilled in the art that the described apparatus may also comprise other functions and structures than those described in Figures and text. It should be appreciated that details of some functions and/or structures may be irrelevant to the actual apparatus and/or method. Therefore, they need not be discussed in more detail here.

This invention relates to simplifying the construct and final assembly of holder apparatus 10 of disposable electrode products. The application field is the measurement device attachment to a disposable, single-use measurement patch in reliable but cheap way. The cost pressure of disposable electrode is very high and presented structure and assembling method may help achieving margins for the end-product.

Figure 1A:
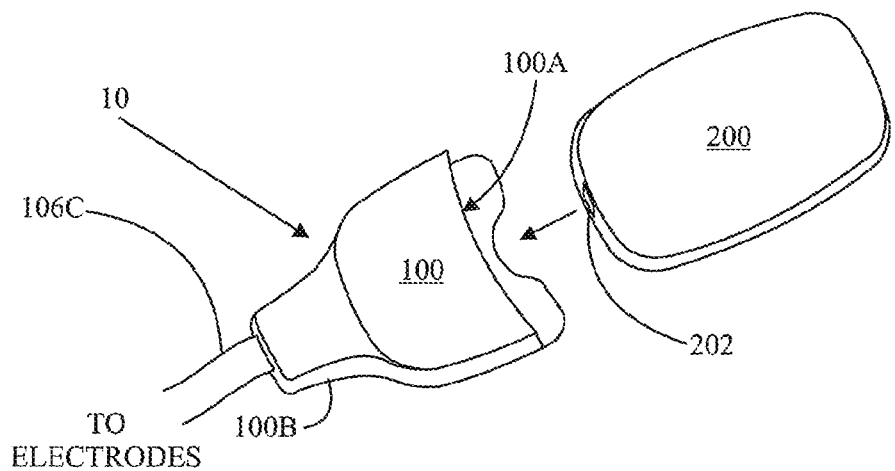
Figure 1B:
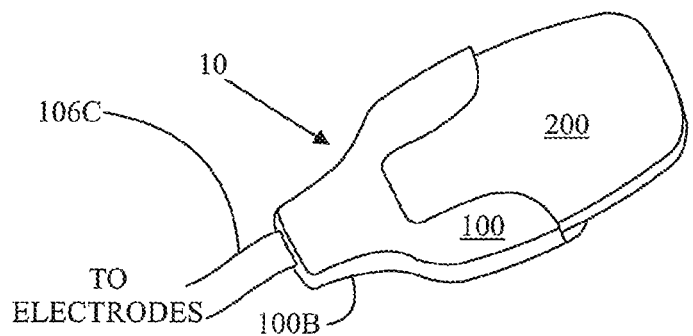

FIGS. 1A and 1B illustrate examples of a holder apparatus 10 for a bio-signal processing device 200. In FIG. 1B, a holder 100 of the holder apparatus 10 has a slit in the front part whereas the holder 100 of FIG. 1A does not have it. The holder 100 may be made of polymer such as plastic. The holder 100 may be made of hard plastic, for example. The hard plastic may be polycarbonate (PC) or the like, for example.

The bio-signal processing device 200 may be an electronic device which may convert an analog bio-signal it receives to a digital bio-signal. The bio-signal processing device 200 may also filter the bio-signal in the analog or in the digital form. Additionally or alternatively, the bio-signal processing device 200 may perform data processing of the bio-signal, and it may also store data of the bio-signal and/or a result of its processing. The bio-signal may be related to body movement, body temperature, heart rate variability, electrocardiogram, electromyogram, electroencephalogram or the like for example.

In FIG. 1A the bio-signal processing device 200 is outside the holder 100. The arrow in FIG. 1A illustrates the feature that the bio-signal processing device 200 can be inserted in the holder 100. In FIG. 1B the bio-signal processing device 200 is inserted in the holder 100.

The walls of the holder 100 follow an outer contour of the bio-signal processing device 200. The pocket 100A is a free space or volume into which a part of the bio-signal processing device 200 fits accurately. A degree of precision with which the surfaces of the bio-signal processing device 200 and the holder 100 are adapted to each other may be high enough to enable operation with one hand or without seeing the actual movement of processing device 200. A friction between an outer surface of the bio-signal processing device 200 and an inner surface of the holder 100 may keep the bio-signal processing device 200 in the holder 100 even under accelerations caused by sport activities or in upside down positions. The fit between the bio-signal processing device 200 and the pocket 100A may be rather tight resulting in a suitable friction and suction force. Polymer material of the holder 100 is also slightly flexible and even stretchable which enables to achieve a suitable tightness and friction and suction force between the holder 100 and the bio-signal processing device 200. The pocket 100A may cover the bio-signal processing device 200 in a continuous hemispherical manner. Alternatively or additionally, the bio-signal processing device 200 may be kept in the holder 100 based on the retention of a connector 106.

Figure 2:
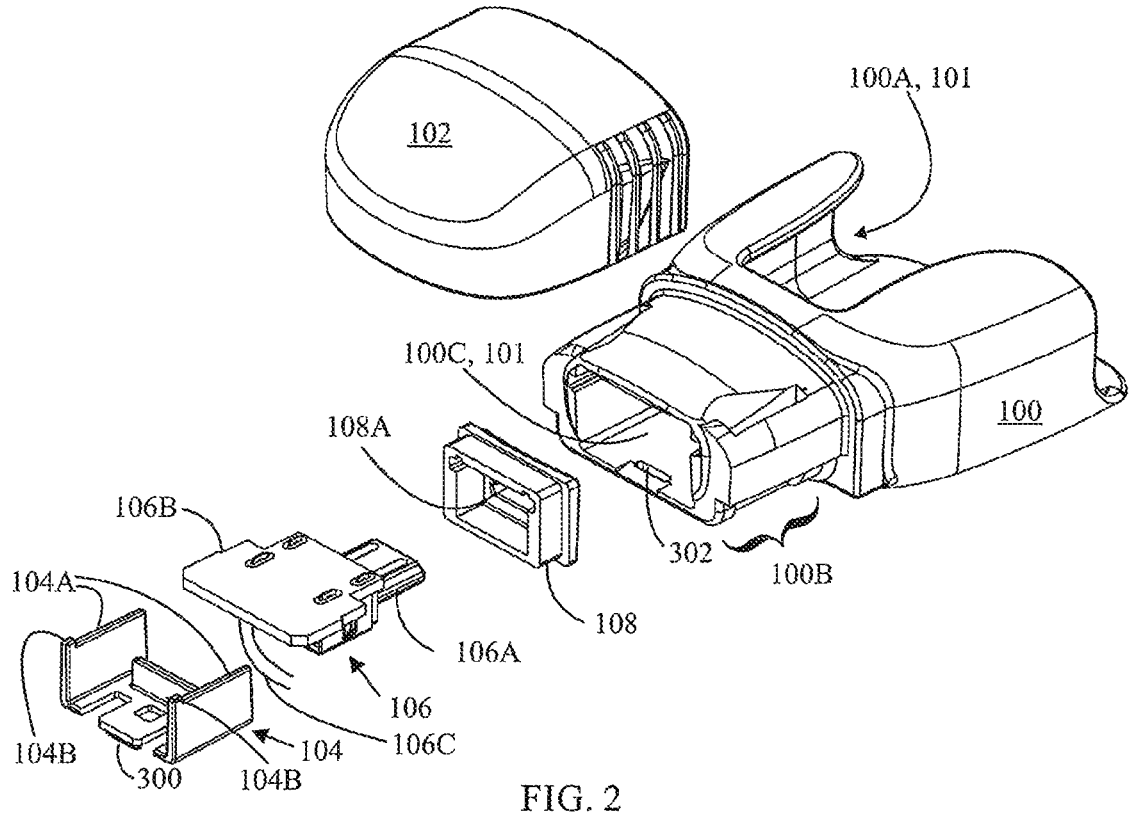
FIG. 2 illustrates an example of parts of the holder apparatus.

FIG. 2 illustrates an example of the holder apparatus 10. The holder 100 comprises a pocket 100A for the bio-signal processing device 200 (see also FIGS. 1A and 1B) and an extension 100B with a hollow 100C. The hollow 100C and the pocket 100A form a continuous cavity 101 through the holder 100.

The holder 100 also includes the connector 106, and an elastic seal 108 with a hole 108A. The elasticity of the elastic seal 108 enables it to be capable of repeatedly deforming to different shapes and sizes which may be important to a seal in general. A shape of the elastic seal 108 is at least approximately matched with a shape of the hollow 100C of the extension 100B at an interface of the pocket 100A and the hollow 100C for easy sealing. The hole 108A of the elastic seal 108 is matched with a shape of an outer surface of the connector 106 for sealing an interface between the connector 106 and the holder 100 while the connector 106 and the elastic seal 108 are within the hollow 100C and the connector 106 is in contact with the elastic seal 108. This is the situation in a ready-made holder apparatus 10, for example.

In an embodiment, the connector 106 may comprise a male electric connector 106A which is inserted through the hole 108A such that it extends to the opposite side of the elastic seal 108. The male connector 106A may be a universal serial bus connector, for example.

Figure 5:
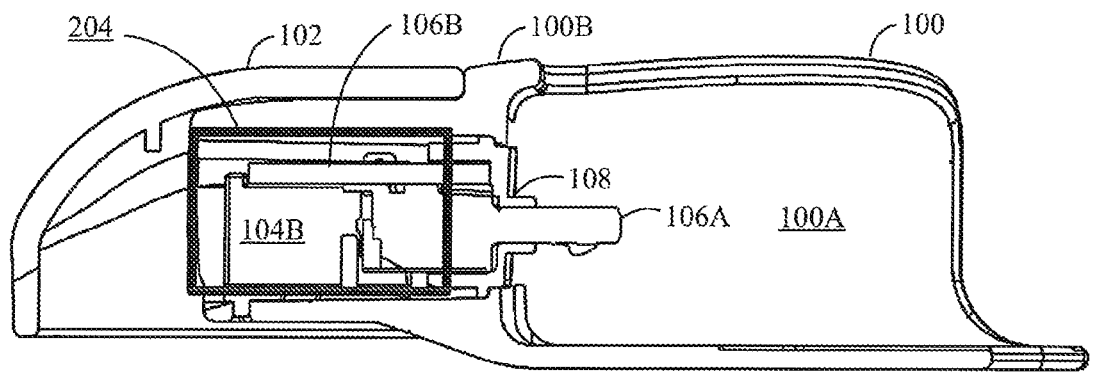
FIG. 5 illustrates an example of an assembled holder apparatus.

As shown in FIG. 5, sealant filler 204 fills the hollow 100C of the extension 100B and is in a physical connection with the connector 106, which is in the hollow 100C. The sealant filler 204 may also be in a physical connection with the elastic seal 108, which is also in the hollow 100C. The sealant filler 204 keeps the connector 106 and the seal 108 immobile within the hollow 100C. This arrangement with the elastic seal 108 and the sealant filler 204 allows, in addition to the stabilizing the arrangement, the connector 106 to mate electrically with a counter-connector 202, which is moved within the cavity 101 in a direction from the pocket 100A toward the hollow 100C. Here the mating means that the connector 106 and the counter-connector 202 join as a pair for forming an electrical and physical connection therebetween.

Figure 3:
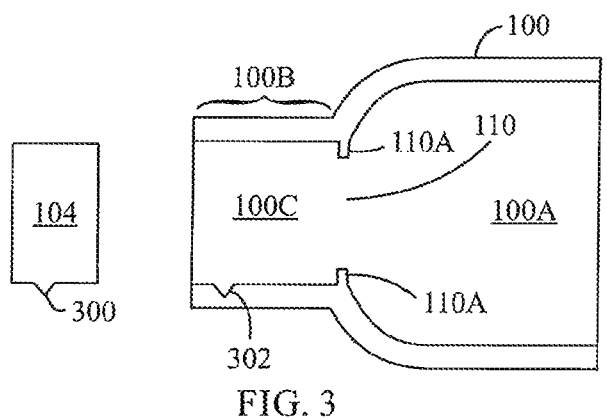
FIG. 3 illustrates an example of locking parts of the holder and a rear part.

In an embodiment, the shape of the elastic seal 108 is matched with the shape of the hollow 100C of the extension 100B. In an embodiment an example of which is shown in FIG. 3, the hollow 100C may comprise an aperture 110 interfacing the pocket 100A, a diameter of the aperture 110 being smaller than a diameter of the hollow 100C. The diameter of the aperture 100 may also be smaller than a diameter of the pocket 100A. The shape of the elastic seal 108 may be matched with the shape of the aperture 110 while the elastic seal 108 being in contact with the aperture 110.

In an embodiment an example of which can be seen FIG. 3, the aperture 110 may be formed with an annular structure 110A at an end of the hollow 100C. The annular structure 110A may form an interface between the hollow 100C and the pocket 100A while still allowing the cavity 101 to continue without interruption through the holder 100.

In an embodiment which is illustrated in FIGS. 2 and 3, the holder apparatus may comprise a rear part 104, and the holder 100 has a first locking part 302 and the rear part 104 has a second locking part 300, the first and the second locking part 300, 302 being configured to mechanically fix together in static positions for locking the holder 100 and the rear part 104 together such that also the connector 106 and the elastic seal 108 therebetween are immobile with respect to each other.

Figure 6:
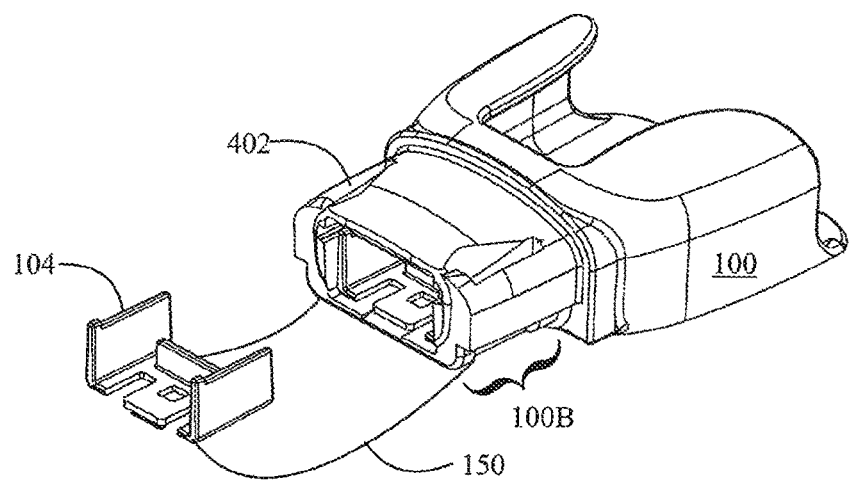
FIG. 6 illustrates an example of a hinge structure.

In an embodiment an example of which is illustrated in FIG. 6, the holder 100 and the rear part 104 are physically connected together through a hinge structure 150. The hinge structure 150 may comprise at least one flexible sheet and/or a plurality of links connected together in a turning manner. Each of the links may be non-flexible but the flexibility may come from the turning connection. The turning connection may be similar to a chain for example.

In an embodiment an example of which is illustrated in FIG. 2, the at least one rail 104A may comprise a heightened structure 104B which becomes in physical contact with connector 106 or the electric circuit 106B when the rear part 104 is inserted into the hollow 100C. In this manner, the at least one rail 104A may prevent the movement of the connector 106 in the hollow 100C because the connector 106 is between the rear part 104 and the seal 108 which are immobile.

The electric circuit may be made on a printed circuit board (PCB), for example. The PCB may hold the electric connector 106A such as micro-USB and some other potential components that may be needed for a proper operation.

In an embodiment an example of which is illustrated in FIG. 2, the holder apparatus 10 may comprise a cover 102 on the extension 100B and the rear part 104. In this manner, the sealant filler 204 may be in contact the cover 102. The cover 102 may protect the extension 100B, the hollow 100C and the rear part 104, the connector 106 and the seal 108 that are in the hollow 100C, and keep the sealant filler 204 in the hollow 100C during its application and also after it has cured. The cure of the sealant filler 204 may mean its hardening from a flowing state to a solid state by a chemical, optical and/or heat process, for example.

Figure 7:
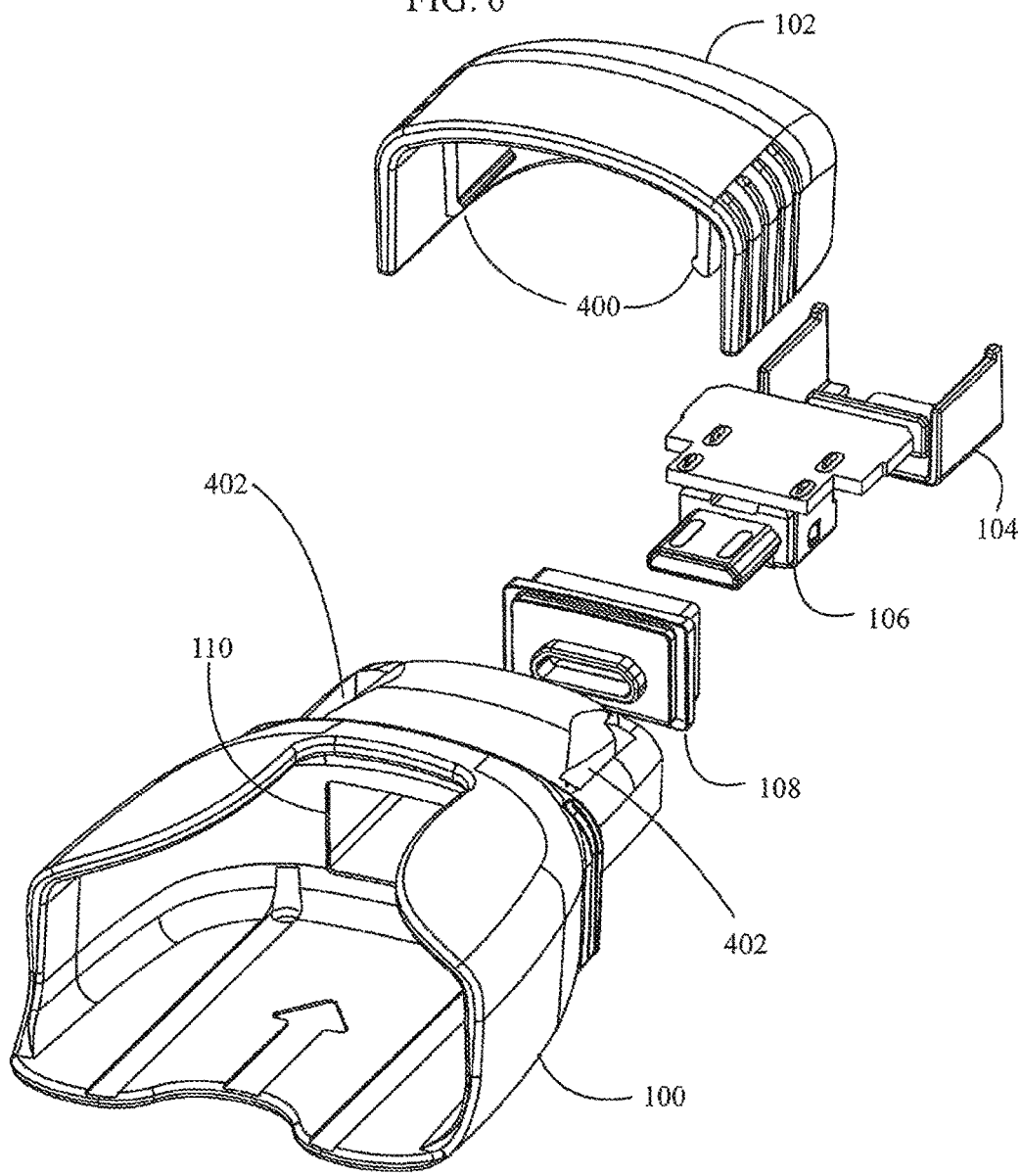
FIG. 7 illustrates an example of a cover with at least one first fixing section and an extension with at least one second fixing section.

In an embodiment an example of which is illustrated in FIG. 7, the cover 102 may comprise at least one first fixing section 400 and the extension 100B may comprise at least one second fixing section 402. The first and the second fixing sections 400, 402 may mechanically fix together in static positions for locking the holder 100 and the cover 102 together such that rear part 104 is immobile thus keeping also the connector 106 and the seal 108 stationary. In embodiment, the first fixing section 400 may comprise an arrow-like extension and the second fixing section 402 may comprise a corresponding hole or cavity. A person skilled in the art is familiar with this kind of locking pairs.

Figure 4:
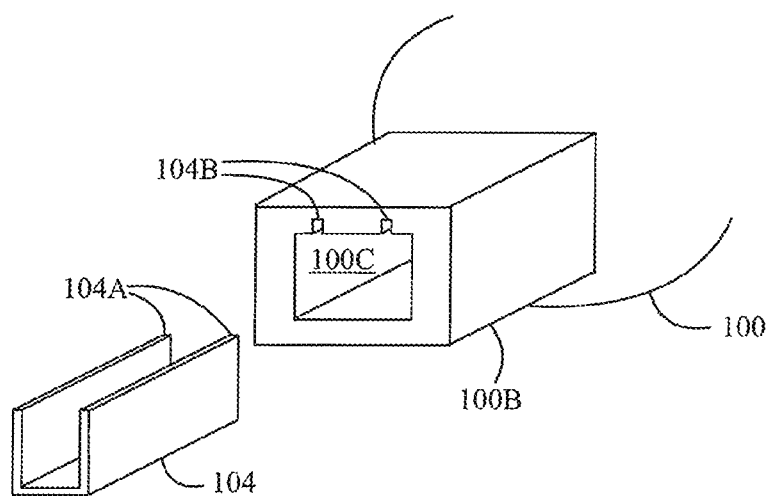
FIG. 4 illustrates an example of rails and grooves of the rear part and the holder.

In an embodiment an example of which is illustrated in FIGS. 2 and 4, the rear part 104 may comprise at least one rail 104A, and the extension 100B may comprise at least one corresponding groove 104B located in the hollow 100C. The at least one rail 104A may move in the at least one groove 104B during assembly of the holder apparatus 10 and the at least one rail 104A stay statically in the at least one groove 104B in the ready-made holder apparatus 10.

In an embodiment an example of which is illustrated in FIGS. 1A, 1B, 2 and 6, the connector 106 may comprise an electric connector 106A and an electric circuit 106B with an electric wire 106C. The electric wire 106C may connect the electric connector 106A with an electrode arrangement (not shown in Figures, but see text "TO ELECTRODES" in FIGS. 1A and 1B) used for bio-signal measurement of a mammal such as a human being. The electrode arrangement may include flexible polyethylene terephthalate (PET) electrodes or the like, for example. The wire 106C may have a connector interface for the electrode arrangement.

What is presented above offers an over-mold-free construct of the holder apparatus on a disposable electrode product, which may measure bio-signals from a body of a mammal. Typically the final electrode assembly consists of multiple parts which are molded together to form the final electro-mechanical part.

Figure 8:
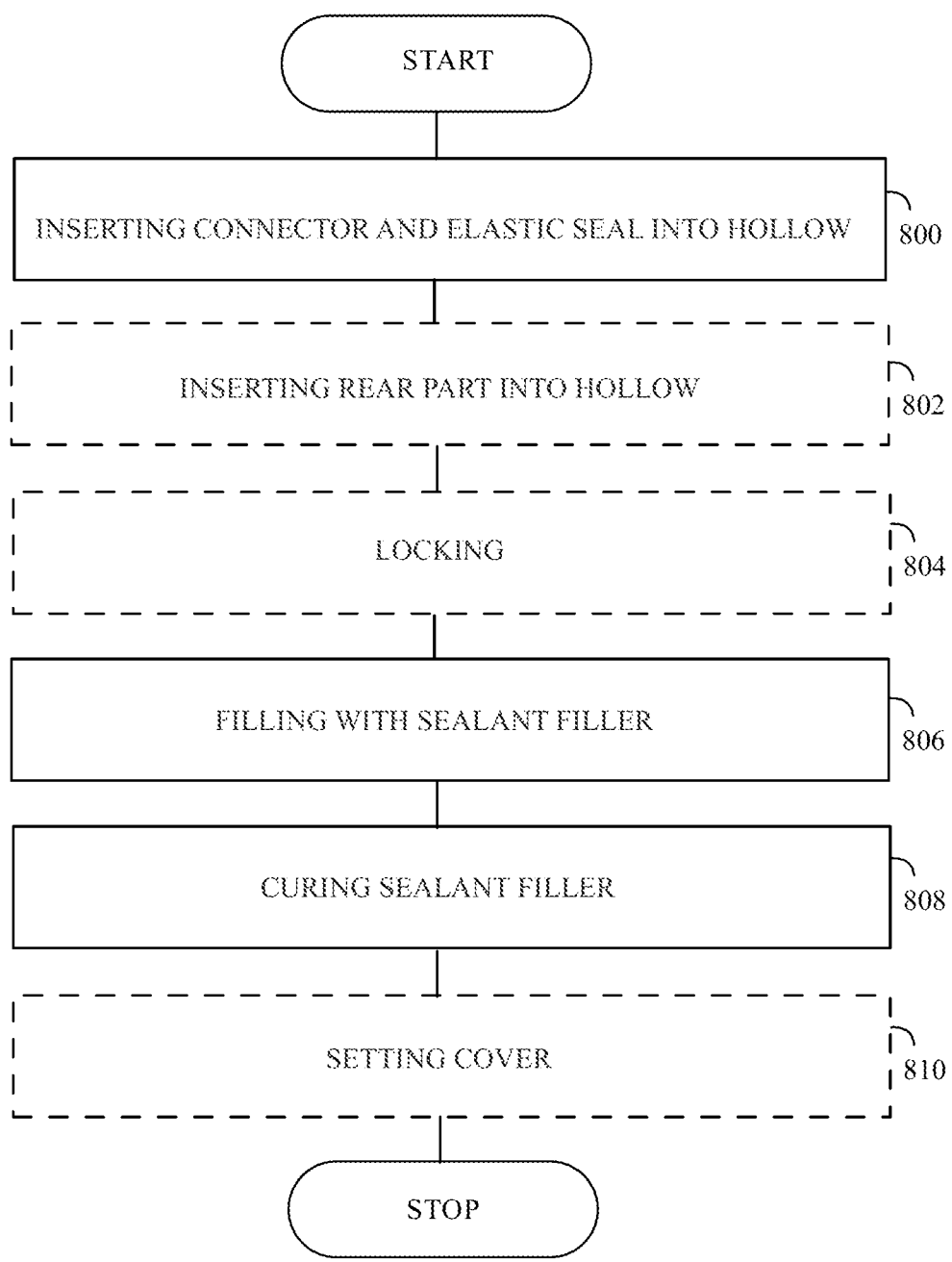
FIG. 8 illustrates of an example of a flow chart of an assembling method.

FIG. 8 is a flow chart of the measurement method. In step 800, a connector 106 and an elastic seal 108 with a hole 108A are inserted into the hollow 100C of the extension 100B of a holder 100, which comprises a pocket 100A for a bio-signal processing device 200, the pocket 100A forming a continuous cavity 101 through the holder 100, where a shape of the elastic seal 108 is matched with a shape of the hollow 100C of the extension 100B at the interface of the hollow 100C and the pocket 100A, and a shape of the hole 108A is matched with a shape of the connector 106 for sealing an interface between the connector 106 and the holder 100 while the connector 106 is in contact with the elastic seal 108.

In step 802 which is optional, a rear part 104 is inserted into the hollow 100C. This may cause the connector 106 and the elastic seal 108 between the rear part 104 and the holder 100 to be immobile with respect to each other.

In step 804 which is optional, the holder 100 and the rear part 104 are locked mechanically together with a first locking part 302 of the holder 100 and the rear part 104 has a second locking part 300 of the rear part 104 for causing also the connector 106 and the elastic seal 108 therebetween to be immobile with respect to each other.

In step 806, the hollow 100C is filled with sealant filler 204, which is a flowing phase, for making the sealant filler 104 to be in physical connection with the connector 106, which is in the hollow 100C.

In step 808, the sealant filler 204 is cured, thus allowing the connector 106 of the holder apparatus 10 to mate electrically with a counter-connector 202 moved within the cavity 101 in a direction from the pocket 100A toward the hollow 100C.

In step 810 which is optional and may be performed before or after step 808, a cover 102 is set on the extension 100B and the rear part 104 for allowing the sealant filler 204 to be in contact the cover 102.

In short, the presented solution enables simplified production flow where over-molding process of a combination of the connector and the electric circuit board for the PET-electrode arrangement can be left out. The same outcome can be achieved as explained above with interlocking the seal 108 and the connector 106 when the PCB is pushed into the extension 100B of the holder 100 of hard plastic. Then the package may be sealed from the behind with the sealant filler 204 such as glue, which may be administered by an automated dispenser, for example. The connector 106 together with the sealant filler 204 can be locked to the holder 100 with the interlocking feature and no complicated outside locking jigs or the like are needed for temporary locking.

It is also possible to create IP67-rated holder apparatus 10 directly on simplified production flow/line where heavy machinery for over-molding is not needed. Also the interlocking feature on the hard plastic holder 100 enables very simplified production jig for final assembly and therefore increases the production speed and improves yield. Note that the holder 100 may also be made of material other than plastic.

One of the following advantage may be achieved based on what is taught in this document:
Streamlined production, final assembly may take place on electrode factory without outsourced molding
Simplified jig structure
Possible to mold device gasket with silicone methods (improved gasket features with right materials)
Possible to use inexpensive glue-material for final assembly (hot glue)
UV-hardened glue for final assembly may be used or avoided
Overall inexpensive solution
No need for expensive over-molding tools
Robust solution
Expandable, can be used in multiple products
Cheap to implement It will be obvious to a person skilled in the art that, as technology advances, the inventive concept can be implemented in various ways. The invention and its embodiments are not limited to the example embodiments described above but may vary within the scope of the claims.

The invention claimed is:

1. A holder apparatus of a bio-signal device, wherein the holder apparatus comprises:
a holder, which comprises a pocket for a bio-signal processing device and an extension with a hollow, the hollow and the pocket forming a continuous cavity through the holder;
a connector, and an elastic seal with a hole, a shape of the elastic seal being matched with a shape of the hollow of the extension at an interface of the pocket and the hollow and a shape of the hole being matched with a shape of the connector for sealing an interface between the connector and the holder while the connector and the elastic seal are within the hollow and the connector is in contact with the elastic seal; and
sealant filler, which is configured to fill the hollow of the extension and be in physical connection with the connector, which is in the hollow against the seal, the elastic seal and the sealant filler allowing the connector to mate electrically with a counter-connector moved within the cavity in a direction from the pocket toward the hollow,
wherein the holder apparatus comprises a rear part, and the holder has a first locking part and the rear part has a second locking part, the first and the second locking parts being configured to mechanically fix together for locking the holder and the rear part together such that the connector and the elastic seal therebetween are immobile with respect to each other, and
wherein the holder apparatus comprises a cover on the extension and the rear part, allowing the sealant filler to be in contact with the cover.

2. The holder apparatus of claim 1, wherein the hollow comprises an aperture interfacing the pocket, a diameter of the aperture being smaller than a diameter of the hollow, and the shape of the elastic seal is matched with the shape of the aperture while the elastic seal being in contact with the aperture.

3. The holder apparatus of claim 1, wherein the holder and the rear part are physically connected together through a hinge structure.

4. The holder apparatus of claim 1, wherein the cover comprises at least one first fixing section and the extension comprises at least one second fixing section, the first and the second fixing sections being configured to mechanically fix together for locking the holder and the cover together such that rear part is immobile to also keep the connector stationary.

5. The holder apparatus of claim 1, wherein the connector comprises an electric connector and an electric circuit with an electric wire.

6. The holder apparatus of claim 1, wherein the bio-signal processing device is configured to be inserted in and removed from the holder, wherein the holder comprises polymer, and wherein the holder includes an electrically conductive contact structure at its rear part for having an electric contact with electrodes and/or sensors that measure bio-signals from a body.

7. A holder apparatus of a bio-signal device, wherein the holder apparatus comprises:
   a holder, which comprises a pocket for a bio-signal processing device and an extension with a hollow, the hollow and the pocket forming a continuous cavity through the holder;
   a connector, and an elastic seal with a hole, a shape of the elastic seal being matched with a shape of the hollow of the extension at an interface of the pocket and the hollow and a shape of the hole being matched with a shape of the connector for sealing an interface between the connector and the holder while the connector and the elastic seal are within the hollow and the connector is in contact with the elastic seal; and
   sealant filler, which is configured to fill the hollow of the extension and be in physical connection with the connector, which is in the hollow against the seal, the elastic seal and the sealant filler allowing the connector to mate electrically with a counter-connector moved within the cavity in a direction from the pocket toward the hollow,
   wherein the holder apparatus comprises a rear part, and the holder has a first locking part and the rear part has a second locking part, the first and the second locking parts being configured to mechanically fix together for locking the holder and the rear part together such that the connector and the elastic seal therebetween are immobile with respect to each other, and
   wherein the rear part comprises at least one rail, and the extension comprises at least one corresponding groove located in the hollow such that the at least one rail is configured to move in the at least one groove during assembly of the holder apparatus and stay statically in the at least one groove in the ready-made holder apparatus.

8. A method of assembling a holder apparatus of a bio-signal electronic device, the method comprising:
   inserting a connector and an elastic seal with a hole into the hollow of the extension of a holder, which comprises a pocket for a bio-signal processing device, the pocket forming a continuous cavity through the holder, wherein a shape of the elastic seal is matched with a shape of the hollow of the extension at an interface of the hollow and the pocket, and a shape of the hole is matched with a shape of the connector for sealing an interface between the connector and the holder while the connector is in contact with the elastic seal;
   filling the hollow with sealant filler, which is in a flowing phase, for making the sealant filler to be in physical connection with the connector, which is within the hollow;
   curing the sealant filler, thus allowing the connector of the holder apparatus to mate electrically with a counter-connector moved within the cavity in a direction from the pocket toward the hollow; and
   setting a cover on the extension and a rear part of the holder apparatus for allowing the sealant filler to be in contact the cover.

9. The method of claim 8, further comprising inserting a rear part into the hollow, and locking mechanically together the holder and the rear part with a first locking part of the holder, wherein the rear part has a second locking part of the rear part for causing the connector and the elastic seal therebetween to be immobile with respect to each other.

10. The method of claim 8, wherein the bio-signal processing device is configured to be inserted in and removed from the holder, wherein the holder comprises polymer, and wherein the holder includes an electrically conductive contact structure at its rear part for having an electric contact with electrodes and/or sensors that measure bio-signals from a body.

* * * * *